US008513437B2

(12) United States Patent
Granot et al.

(10) Patent No.: US 8,513,437 B2
(45) Date of Patent: Aug. 20, 2013

(54) PYRROLIDINO-1,4-NAPHTHOQUINONE DERIVIATIVES AND THEIR USE FOR TREATING MALIGNANCIES AND CARDIOVASCULAR DISEASES

(75) Inventors: Yossi Granot, Omer (IL); Shmuel Bittner, Omer (IL)

(73) Assignee: Ben Gurion University of the Negev Research and Development Authority, Beer Sheva (IS)

( * ) Notice: Subject to any disclaimer, the term of this patent is extended or adjusted under 35 U.S.C. 154(b) by 1794 days.

(21) Appl. No.: 11/658,304

(22) PCT Filed: Jul. 21, 2005

(86) PCT No.: PCT/IL2005/000783
§ 371 (c)(1),
(2), (4) Date: Jan. 23, 2007

(87) PCT Pub. No.: WO2006/011136
PCT Pub. Date: Feb. 2, 2006

(65) Prior Publication Data
US 2008/0300274 A1    Dec. 4, 2008

(30) Foreign Application Priority Data

Jul. 26, 2004    (IL) .......................................... 163216

(51) Int. Cl.
*C07D 207/00*    (2006.01)
*C09B 1/00*    (2006.01)

(52) U.S. Cl.
USPC .......................................... 548/407; 548/529

(58) Field of Classification Search
USPC .................................................. 548/407, 529
See application file for complete search history.

(56) References Cited

U.S. PATENT DOCUMENTS

| 6,130,235 A | 10/2000 | Mavunkel et al. |
| 6,495,582 B1 | 12/2002 | Hale et al. |
| 6,503,930 B1 | 1/2003 | Hanson et al. |

FOREIGN PATENT DOCUMENTS

JP    08-113555    5/1996

OTHER PUBLICATIONS

Stephen N. Falling & Henry Rapoport, Routes to Mitomycins, Applications of Iminium Salts to the Synthesis of Napthoquinone Mitosene Analogues, 45 J Org. Chem. 1260 (1980).*
Prativa Shreshta, et al, On the Synthesis of Napthoquinonyl Heterocyclic Amino Acids, 1996(12) Synthesis 1468.*
George A. Patani & Edmond J. LaVoie, Bioisosterism: A Rational Approach in Drug Design, 96 Chem. Rev. 3147, 3148 (1996).*
International Preliminary Report on Patentability of the corresponding PCT application—5 pages, Jul. 10, 2006.

* cited by examiner

*Primary Examiner* — Sean Basquill
(74) *Attorney, Agent, or Firm* — Roach Brown McCarthy & Gruber P.C.; Kevin D. McCarthy (57) ABSTRACT

The invention provides pyrrolidino-substituted 1,4-naphthoquinone derivatives that modulate the activity of protein kinases, and it relates to the use of the derivatives in pharmaceutical compositions for treating cardiovascular disorders and malignancies. The invention particularly provides medicaments for treating disorders associated with MAPKs signaling, ERKs signaling, p38 signaling, and JNKs signaling.

2 Claims, 4 Drawing Sheets

PYRROLIDINO-1,4-NAPHTHOQUINONE DERIVIATIVES AND THEIR USE FOR TREATING MALIGNANCIES AND CARDIOVASCULAR DISEASES

FIELD OF THE INVENTION

The present invention relates to naphthoquinone derivatives that modulate the activity of protein kinases in cells, and to the use of said derivatives in pharmaceutical compositions, especially for treating cardiovascular disorders and malignancies. The invention is also directed to a method for producing said compounds.

BACKGROUND OF THE INVENTION

Protein kinases—enzymes phosphorylating proteins—play central role in cell signaling and cell division, and are therefore prominent therapeutic targets. Hundreds of protein kinases have been identified, differing in substrate specificity, the way of activation, and tissue occurrence or subcellular localization, wherein said protein kinases are members of multiple simultaneous pathways which may be independent or interlinked; consequently, it is difficult to target a specific enzyme involved in a certain pathological state.

Among the protein kinases, the super-family of mitogen activated protein kinases (MAPKs) seems to play a major role in signal transduction pathways. The members of the MAPKs family are involved in the regulation of a large variety of cellular processes, such as cell growth, differentiation, development, programmed cell death (apoptosis) and survival. ERKs (½) (extracellular signal-regulated kinases) are generally associated with cell proliferation and survival, while JNKs (c-Jun N-terminal kinases) and p38-MAPKs are responsible to cellular stress, such as hyperosmotic shock, metabolic stress or protein synthesis inhibitors, UV radiation, heat shock, cytokines and ischemia, all leading to apoptotic response. U.S. Pat. No. 6,495,582 discloses certain isoxazoles as inhibitors of ERKs, and their use for treating an ERK-mediated disease, whereas the recited disorders comprise nearly all existing diseases. U.S. Pat. No. 6,503,930 discloses novel pyrazoles and their use for treating the disorders mediated by p38, reciting the diseases related to inflammation. U.S. Pat. No. 6,130,235 discloses certain piperazines or piperidines inhibiting p38, and their use for treating a condition associated with p38 kinase.

An additional signaling pathway that plays a crucial role in the expression of stress-responsive genes and survival in a variety of cells and organs is the JAKs/STATs signaling pathway. STATs (signal transducers and activators of transcription) are a family of transcription factors that are activated by the JAK family of kinases. When cells encounter various extracellular ligands, such as interferons and EGF, the STATs promote rapid induction of genes.

Cardiovascular diseases and malignancies are the principal cause of death in the developed countries. Many protein kinases have been implicated in various aspects of cardiac pathologies and cancer pathogenesis. Cardiovascular diseases are characterized by diverse cellular abnormalities. These abnormalities may be stimulated by a variety of hormones and growth factors, whose signals are amplified by cascades involving protein kinases as PKCs and the MAPKs super-family. Recent evidence suggests that activation of MAPKs super-family plays a key role in the pathogenesis of various processes in the heart, e.g. in myocardial hypertrophy and its transition to heart failure, in ischemic and reperfusion injury, as well as in cardioprotection induced by preconditioning. Modulation of MAPKs activity may represent a potential therapeutic target providing protection on the myocardium by way of either inhibition of deleterious pathways and shifting the balance toward cell survival or by activation of pathways participating in the cardioprotective cascade. The JAKs/STATs signaling pathway was also found to participate in the ischemia/reperfusion process and the cardioprotection following preconditioning. However, the complexity of these systems lead to contradictory data and conclusions, and in some cases it is even unclear if the therapeutic goal is to inhibit or to activate a certain kinase. What seems to be needed most are new agents that could selectively inhibit detrimental pathways and activate the benign ones [e.g.: Vlahos C. J. et al.: Nature Reviews, Drug Discovery 2 (2003) 99-113; Bolli R. et al.: Trends Cardiovasc. Med. 13 (2003) 72-9].

It is therefore an object of this invention to provide compounds capable of signal transduction modulating protein kinases such as kinases from MAPKs family, JAKs/STATs and Akt for use as medicaments in treating cardiovascular diseases. Such medicament should, e.g., help in the survival of cardiomyocytes—"the good cells", and should inhibit the proliferation of vascular smooth muscle (VSM) cells—"the bad cells". An ideal compound would, for example, increase ERKs signaling pathway to induce cardioprotective functions and survival, and inhibit p38 and/or JNK/SAPK activation to reduce cardiomyocyte death, and further it would stimulate p38 and/or JNK/SAPK activation and inhibit ERKs signaling in said VSM cells; thus, the survival of cardiomyocytes would be enhanced, and the uncontrolled proliferation of VSM cells would be reduced in atherosclerosis, stenosis or resteriosis diseases. Enhancement of the ERKs signaling pathway and other survival pathways may be also beneficial for cardiomyocyte survival in diseases such as myocardial infarction.

The MAPKs family and the JAKs/STATs pathway may also offer new opportunities in development of novel selective anti-cancer drugs. Numerous solid tumors are known to express constitutive levels of phosphorylated ERK1 and ERK2 that activate variety of transcription factors. Mutation in Ras and Raf were also identified in a range of human tumors. Therefore, the Ras-Raf-MEK-ERKs signaling cascade may be an important target in cancer therapies [Hilger R. et al.: Onkologie 25(6) (2002) 511-8]. For some cancers, especially those of hematopoietic origin, the p38 and JNKs pathways may be targeted. Significant percentage of human tumors exhibits the constitutive activation of the MAPKs pathway [Hoshino, R. et al.: Oncogene 18(3) (1999) 813-22], suggesting that a single agent could concurrently exploit more than one of these processes, and potentially impair the tumor survival. Thus, therapeutic approaches to cancer treatment may involve slowing the tumor growth, inhibiting the invasion and metastasis, inducing tumor cell death, or promoting tumor differentiation. The STATs proteins are also known to participate in cellular transformation, tumorigenesis and oncogenesis. Subsequent work showed that in a number of tumor-derived cell lines, the STATs, particularly STAT3, are required to maintain a transformed phenotype. STAT5 is also commonly found to be constitutively activated in certain malignancies, especially leukemia and lymphomas.

[Bromberg J.: JCI 109 (2002) 1139-42, Luo C. et al.: Drug Discovery Today 9 (2004) 268-75].

Therefore, the present invention further aims at providing drugs for treating malignancies by modulation the activity of protein kinases such as MAPKs family, JAKs/STATs and Akt through either inhibiting the deleterious pathways and shifting the balance toward the cell apoptosis, or by activating the pathways participating in the tumor differentiation.

It is an object of the invention to provide novel compounds capable of modulating protein kinase systems, the compounds being pyrrolidino-substituted 1,4-naphthoquinone derivatives.

Still another object of the present invention is to provide pyrrolidino-substituted 1,4-naphthoquinone derivatives capable of inhibiting or stimulating the MAPKs activity in cardiomyocytes, VSM cells, or malignant cells.

Other objects and advantages of present invention will appear as description proceeds.

SUMMARY OF THE INVENTION

The present invention provides a compound of formula I:

wherein $R_1$ is selected from H, heterocycle comprising from 4 to 6 carbon atoms, alkoxy, $C_1$-$C_6$alkylamino, heterocycle comprising 1 or 2 nitrogen atoms and from 4 to 6 carbon atoms; $R_2$ is selected from H, $C_1$-$C_6$alkyl, aryl comprising from 6 to 14 carbon atoms, and aralkyl comprising from 7 to 18 carbon atoms; and $R_3$ and $R_4$ groups are independently selected from H, hydroxyl, fluoro, chloro, bromo, iodo, alkoxycarbonyl, alkoxy, amino, nitro, $C_1$-$C_{16}$alkyl, $C_1$-$C_6$alkoxy, aryl comprising from 6 to 14 carbon atoms, aralkyl comprising from 7 to 18 carbon atoms, $C_1$-$C_6$alkylamine, dialkylamine wherein two alkyls are independently $C_1$-$C_6$alkyls, and benzoylamino wherein said benzoyl is optionally substituted with hydroxyl, fluoro, chloro, bromo, iodo, amino, $C_1$-$C_6$alkyl, and $C_1$-$C_6$alkoxy. An example of $C_1$-$C_6$alkylamino is —$NH_2$—$CH_2$ or 1-piperidino; an example of amino$C_1$-$C_6$alkyl is —$CH_2$—$NH_2$. Preferably, a molecule of structure I, in which $R_1$ is either a substituted or a non-substituted pyrrolydine group, or either a substituted or a non-substituted piperidine group, $R_2$ is H and $R_3$ and $R_4$ groups are independently selected from H, hydroxyl, fluoro, chloro, bromo, iodo, alkoxycarbonyl, alkoxy, amino, nitro, $C_1$-$C_{16}$alkyl, $C_1$-$C_6$alkoxy, aryl comprising from 6 to 14 carbon atoms, aralkyl comprising from 7 to 18 carbon atoms, $C_1$-$C_6$alkylamine, dialkylamine, wherein two alkyls are independently $C_1$-$C_6$alkyls, and benzoylamino wherein said benzoyl is optionally substituted with hydroxyl, fluoro, chloro, bromo, iodo, amino, $C_1$-$C_6$alkyl, and $C_1$-$C_6$ alkoxy. Most preferably, a molecule of structure I, in which $R_1$ is a pyrrolydine group, $R_2$ and $R_3$ are H, and $R_4$ is either a methyl group at para position, or an hydroxyl group at para position (TW85 and TW96, respectively).

The present invention provides a compound of formula II:

wherein the proline moiety is either L isomer or D isomer or a mixture of L isomer and D isomer, $R_1$ is selected from H, fluoro, chloro, bromo, iodo, alkoxy, $C_1$-$C_6$alkylamino, heterocycle comprising 1 or 2 nitrogen atoms and from 4 to 6 carbon atoms; and $R_2$ is selected from H, $C_1$-$C_{16}$alkyl, $C_1$-$C_6$alkoxy, aryl comprising from 6 to 14 carbon atoms, aralkyl comprising from 7 to 18 carbon atoms, $C_1$-$C_6$alkylamine, dialkylamine wherein two alkyls are independently $C_1$-$C_6$alkyls, and benzoylamino wherein said benzoyl is optionally substituted with hydroxyl, fluoro, chloro, bromo, iodo, amino, $C_1$-$C_6$alkyl, and $C_1$-$C_6$alkoxy. Preferably, compound of formula II in which $R_1$ is an halogen atom and $R_2$ is either H or an alkyl group. Most preferably, compound of formula II in which $R_1$ is Cl atom and $R_2$ is methyl group (EH-48).

The invention also relates to a pharmaceutical formulation comprising at least one compound of formula I or formula II. The invention further relates to the use of a compound of formula I or formula II, or a pharmaceutically acceptable salt thereof, in the preparation of a medicament for treating cardiovascular disorders and malignancies. Said cardiovascular disorders are preferably selected from the group consisting of restenosis, cardiomegaly, atherosclerosis, myocardial infarction, or congestive heart failure. Said malignancies are relate to all potential malignancies.

The invention is further directed to a method for treating cardiovascular disorders and malignancies comprising the steps of i) providing at least one compound of formula I or formula II as defined above, or a pharmaceutically acceptable salt thereof; and ii) administering said compound or its salt to a patient in need of the treatment.

The invention is also directed to a process of preparing a compound of formula I:

wherein $R_1$ is selected from H, heterocycle comprising from 4 to 6 carbon atoms, alkoxy, $C_1$-$C_6$alkylamino; $R_2$ is selected from H, $C_1$-$C_6$alkyl, aryl comprising from 6 to 14 carbon atoms, and aralkyl comprising from 7 to 18 carbon atoms; and $R_3$ and $R_4$ groups are independently selected from H, hydroxyl, fluoro, chloro, bromo, iodo, alkoxycarbonyl, alkoxy, amino, nitro, $C_1$-$C_{16}$alkyl, $C_1$-$C_6$alkoxy, aryl comprising from 6 to 14 carbon atoms, aralkyl comprising from 7 to 18 carbon atoms, $C_1$-$C_6$alkylamine, dialkylamine wherein two alkyls are independently $C_1$-$C_6$alkyls, and benzoylamino wherein said benzoyl is optionally substituted with hydroxyl, fluoro, chloro, bromo, iodo, amino, $C_1$-$C_6$alkyl, and $C_1$-$C_6$alkoxy. Preferably, molecule of structure I, in which $R_1$ is a substituted or a non-substituted pyrrolydine group, or a substituted or a non-substituted piperidine group, $R_2$ is H and $R_3$ and $R_4$ groups are independently selected from H, hydroxyl, fluoro, chloro, bromo, iodo, alkoxycarbonyl, alkoxy, amino, nitro, $C_1$-$C_{16}$alkyl, $C_1$-$C_6$alkoxy, aryl comprising from 6 to 14 carbon atoms, aralkyl comprising from 7 to 18 carbon atoms, $C_1$-$C_6$alkylamine, dialkylamine wherein two alkyls are independently $C_1$-$C_6$alkyls, and benzoylamino wherein said benzoyl is optionally substituted with hydroxyl, fluoro, chloro, bromo, iodo, amino, $C_1$-$C_6$alkyl, and $C_1$-$C_6$alkoxy. Most preferably, a molecule of structure I, in which $R_1$ is a pyrrolydine group, $R_2$ and $R_3$ are H, and $R_4$ is either a methyl group at para position, or an hydroxyl group at para position (TW85 and TW96, respectively).

wherein compound of formula I is obtained by a two-stage reaction, the first stage comprising the reaction of a compound having the following structure:

wherein $R_1$ is Cl, with a compound having the following structure:

wherein $R_1$, $R_2$, $R_3$, and $R_4$ have the meaning as defined above, and the second stage comprising the reaction of the product of the first stage with pyrrolidine having the following structure:

The invention is also directed to a process of preparing a compound of formula II:

wherein the proline moiety is either L isomer or D isomer or a mixture of L isomer and D isomer, $R_1$ is selected from H, fluoro, chloro, bromo, iodo, alkoxy, $C_1$-$C_6$alkylamino, heterocycle comprising 1 or 2 nitrogen atoms and from 4 to 6 carbon atoms; and $R_2$ is selected from H, $C_1$-$C_{16}$alkyl, $C_1$-$C_6$alkoxy, aryl comprising from 6 to 14 carbon atoms, aralkyl comprising from 7 to 18 carbon atoms, $C_1$-$C_6$alkylamine, dialkylamine wherein two alkyls are independently $C_1$-$C_6$alkyls, and benzoylamino wherein said benzoyl is optionally substituted with hydroxyl, fluoro, chloro, bromo, iodo, amino, $C_1$-$C_6$alkyl, and $C_1$-$C_6$alkoxy. Preferably, compound of formula II in which $R_1$ is an halogen atom, and $R_2$ is either H or an alkyl group, and most preferably, compound of formula II in which $R_1$ is Cl atom and $R_2$ a methyl group (EH-48), wherein compound of formula II is obtained by reacting compound having the following structure:

wherein $R_1$ is Cl, with a pyrrolidine derivative having the structure:

wherein the proline methyl ester is either L isomer or D isomer or a mixture of L isomer and D isomer, $R_2$ is selected from H, $C_1$-$C_{16}$alkyl, $C_1$-$C_6$alkoxy, aryl comprising from 6 to 14 carbon atoms, aralkyl comprising from 7 to 18 carbon atoms, $C_1$-$C_6$alkylamine, dialkylamine wherein two alkyls are independently $C_1$-$C_6$alkyls, and benzoylamino wherein said benzoyl is optionally substituted with hydroxyl, fluoro, chloro, bromo, iodo, amino, $C_1$-$C_6$alkyl, and $C_1$-$C_6$alkoxy. Preferably, $R_2$ is either H or an alkyl group, and most preferably $R_2$ is a methyl group.

The invention provides a method of modulating MAPKs activity, comprising contacting a MAPK enzyme with a compound of formula I and/or formula II, wherein said modulating occurs in vitro or in vivo. The method relates to the inhibition or stimulation of MAPK signaling system or of some of its regulation elements.

BRIEF DESCRIPTION OF THE DRAWINGS

The above and other characteristics and advantages of the invention will be more readily apparent through the following examples, and with reference to the appended drawings, wherein:

FIG. 1. is a Western immunoblot showing ERKs and p38-MAPK phosphorylation.

FIG. 4. shows apoptotic response in HT29 colon carcinoma cells after the treatment with TW69; 4A shows nuclei with fragmented DNA, stained with acridine orange and ethidium bromide; 4B shows FACS analysis of propidium iodide staining assay, wherein the graphs represent the relative number of cells versus the relative amount of DNA in the cells (2N corresponding to normal cells, 4N to proliferating cells, and less than 2N to apoptotic cells);

FIG. 6. shows cardiomyocytes proliferation following injection of compound of formula II in-vivo into normal rat heart; 6A shows PCNA staining in rat heart tissue (arrows); 6B shows summary of the results related to the treatment of the 4 groups.

DETAILED DESCRIPTION OF THE INVENTION

It has now been found that certain pyrrolidino-substituted 1,4-naphthoquinone derivatives strongly modulate MAPKs signaling pathways, affect viability of cardiomycetes and VSM cells, and increase apoptosis in certain cancer cells.

A variety of compounds has been synthesized, of general formula I:

I wherein $R_1$ is selected from H, heterocycle comprising from 4 to 6 carbon atoms, alkoxy, $C_1$-$C_6$alkylamino; $R_2$ is selected from H, $C_1$-$C_6$alkyl, aryl comprising from 6 to 14 carbon atoms, and aralkyl comprising from 7 to 18 carbon atoms; and $R_3$ and $R_4$ groups are independently selected from H, hydroxyl, fluoro, chloro, bromo, iodo, alkoxycarbonyl, alkoxy, amino, nitro, $C_1$-$C_{16}$alkyl, $C_1$-$C_6$alkoxy, aryl comprising from 6 to 14 carbon atoms, aralkyl comprising from 7 to 18 carbon atoms, $C_1$-$C_6$alkylamine, dialkylamine wherein two alkyls are independently $C_1$-$C_6$alkyls, and benzoylamino wherein said benzoyl is optionally substituted with hydroxyl, fluoro, chloro, bromo, iodo, amino, $C_1$-$C_6$alkyl, and $C_1$-$C_6$alkoxy. Preferably, molecule of structure I, in which $R_1$ is a substituted or a non-substituted pyrrolydine group or a substituted or a non-substituted piperidine group, $R_2$ is H and $R_3$ and $R_4$ groups are independently selected from H, hydroxyl, fluoro, chloro, bromo, iodo, alkoxycarbonyl, alkoxy, amino, nitro, $C_1$-$C_{16}$alkyl, $C_1$-$C_6$alkoxy, aryl comprising from 6 to 14 carbon atoms, aralkyl comprising from 7 to 18 carbon atoms, $C_1$-$C_6$alkylamine, dialkylamine wherein two alkyls are independently $C_1$-$C_6$alkyls, and benzoylamino wherein said benzoyl is optionally substituted with hydroxyl, fluoro, chloro, bromo, iodo, amino, $C_1$-$C_6$alkyl, and $C_1$-$C_6$alkoxy, and most preferably, a molecule of structure I, in which $R_1$ is a pyrrolydine group, $R_2$ and $R_3$ are H, and $R_4$ is either a methyl group at para position, or an hydroxyl group at para position (TW85 and TW96, respectively).

Some of the compounds were prepared by first reacting the following two compounds:

wherein $R_1$, $R_2$ and $R_3$ have the same meaning as defined above, wherein the reaction was performed in ethanol at room temperature for 16-24 hours, and the second stage being reacting the product of the first stage with a pyrrolidine derivative as defined above, the second stage comprising mixing the product of the first stage and the pyrrolidine derivative at room temperature for one hour and chromatographing the reaction mixture.

A variety of compounds have been synthesized, of general formula II:

II wherein the proline moiety is either L isomer or D isomer or a mixture of L isomer and D isomer, $R_1$ is selected from H, fluoro, chloro, bromo, iodo, alkoxy, $C_1$-$C_6$alkylamino, heterocycle comprising 1 or 2 nitrogen atoms and from 4 to 6 carbon atoms; and $R_2$ is selected from H, $C_1$-$C_{16}$alkyl, $C_1$-$C_6$alkoxy, aryl comprising from 6 to 14 carbon atoms, aralkyl comprising from 7 to 18 carbon atoms, $C_1$-$C_6$alkylamine, dialkylamine wherein two alkyls are independently $C_1$-$C_6$alkyls, and benzoylamino wherein said benzoyl is optionally substituted with hydroxyl, fluoro, chloro, bromo, iodo, amino, $C_1$-$C_6$alkyl, and $C_1$-$C_6$alkoxy. Preferably, compound of formula II in which $R_1$ is an halogen atom and $R_2$ is either H or an alkyl group, and most preferably, compound of formula II in which $R_1$ is Cl atom and $R_2$ is methyl group, wherein compound of formula II is obtained by reacting compound having the following structure:

wherein $R_1$ is Cl, with a pyrrolidine derivative having the structure:

wherein the proline methyl ester is either L isomer or D isomer or a mixture of L isomer and D isomer, $R_2$ is selected from H, $C_1$-$C_{16}$alkyl, $C_1$-$C_6$alkoxy, aryl comprising from 6 to 14 carbon atoms, aralkyl comprising from 7 to 18 carbon atoms, $C_1$-$C_6$alkylamine, dialkylamine wherein two alkyls are independently $C_1$-$C_6$alkyls, and benzoylamino wherein said benzoyl is optionally substituted with hydroxyl, fluoro, chloro, bromo, iodo, amino, $C_1$-$C_6$alkyl, and $C_1$-$C_6$alkoxy. Preferably, $R_2$ is either H or an alkyl group, and most preferably $R_2$ is a methyl group, wherein molecule of structure II was prepared by reacting 1,4-dichloronaphthoquinone with a pyrrolidine derivative as defined above, the reaction carried out in ethanol for 24 hours at room temperature and the reaction mixture separated by a chromatographic column.

The effect of the prepared compounds on MAPK pathways was examined, using primary cardiomyocytes derived from neonatal rats, primary vascular smooth muscle (VSM) cells derived from rat aorta, and human colon carcinoma HT29 cells. The power of the compounds to stimulate the formation of active proteins of MAPKs super-family, namely ERK, p38-MAPK, and STAT3, were evaluated with specific antibodies against the Phosphorylated sites; and the cell viability and apoptosis were evaluated by known methods. The decrease of viability was characterized by $ID_{50}$, the concentration causing 50% decrease in the number of viable cells.

The results showed that compounds of formula I had a strong effect on MAPKs pathways at concentrations of several μM and lower. The effect was found to be specific to cell type. E.g., compounds TW96 and TW69 did not injure the cardiomyocytes at concentrations killing VSM cells.

Further, if was found that compounds of formula I stimulated selectively different MAPKs pathways both in VSM cells and in cardiomyocytes. E.g., compounds TW69 and TW85 induced the formation of phosphorylated ERKs protein in cardiomyocytes without inducing the formation of phosphorylated p38 protein.

The results further showed that compounds of formula I were capable of stimulating p38 without activating ERK in HT29 human colon carcinoma cells. E.g., compound TW96 stimulated mostly the p38-MAPKs signaling pathway, and therefore may be used to increase the apoptotic response and death in colon carcinoma cells. As noted above, the ERKs signaling pathways participate in the cell proliferation, and p38-MAPKs in apoptosis, so that the compounds of the invention may prevent uncontrolled cell proliferation.

In a preferred embodiment of the invention, the compound of formula I has the following formula:

wherein $R_1$ is a substituted or a non-substituted pyrrolydine group or a substituted or a non-substituted piperidine group; and $R_3$ and $R_4$ are independently selected from H, hydroxyl, fluoro, chloro, bromo, iodoo, amino, nitro, $C_1$-$C_6$alkyl, $C_1$-$C_6$alkoxy, aryl comprising from 5 to 14 carbon atoms, aralkyl comprising from 8 to 18 carbon atoms, $C_1$-$C_6$alkylamine, dialkylamine wherein two alkyls are independently $C_1$-$C_6$alkyls, and benzoylamino wherein said benzoyl is optionally substituted with hydroxyl, fluoro, chloro, bromo, iodoo, amino, $C_1$-$C_6$alkyl, and $C_1$-$C_6$alkoxy. Most preferably, a molecule of structure I, in which $R_1$ is a pyrrolydine group, $R_2$ and $R_3$ are H, and $R_4$ is either a methyl group at para position, or an hydroxyl group at para position (TW85 and TW96, respectively)

In another preferred embodiment of the invention, the compound of formula II has the following formula:

II wherein the proline moiety is either L isomer or D isomer or a mixture of L isomer and D isomer, $R_1$ is Cl; and $R_2$ is an alkyl group. Most preferably $R_1$ is Cl and $R_2$ is methyl group.

The compounds of the invention have strong effects on MAPKs pathways. Their ability to enhance ERKs signaling pathway to induce cardioprotective functions and survival will be investigated, as well as their capability of inhibiting p38 activation to reduce cardiomyocytes death. In VSM cells, these compounds of the invention will stimulate p38 activation and will inhibit ERKs signaling; therefore these compounds will be able to protect cardiomycetes and to reduce the uncontrolled proliferation of VSM cells, thus providing the treatment of atherosclerosis, stenosis or restenosis diseases, and myocardial infarction. In cardiomyocyte cells, these compounds of the invention will stimulate ERKs signaling pathway; therefore these compounds will be able to protect cardiomyocytes, enhance cardiomyocyte survival and proliferation, thus providing the treatment of myocardial infarction and cardiac failure.

The compounds of the invention modulate MAPKs activity in carcinoma cells, while inhibiting signals in the pathways related to the increased proliferation, and enhancing signals in the pathways related to apoptosis, thus providing the treatment of malignancies.

The results indicate that formula I and formula II provide efficient compounds for therapy in the field of cardiovascular diseases and malignancies. The compounds may also serve as lead compounds for developing still more efficient medicaments, possibly by means of rational drug design. However, the preferred compounds themselves, as exampled herein, can serve in the preparation of medicaments for treating disorders associated with activity of protein kinases signaling pathways such as the MAPKs signaling pathway.

The invention provides a pharmaceutical composition comprising at least one compound of formula I and formula II, and additives selected from pharmaceutically acceptable adjuvant, excipient, carrier or diluents, and optionally another pharmaceutically active substance selected from anti-arteriosclerotic, antihypertensive, anti-inflammatory, cardio-protective, vasodilatory, antineoplastic, antibacterial, and antiviral.

In one aspect, the present invention enables to modulate MAPKs signaling system, inhibiting some of the regulation elements of the said system and stimulating others. Said modulation relates both to in vitro methods which can be used in characterizing kinases and in searching for new ones, and to in vivo methods which can be used for animal model studies and for treating disorders related to the said signaling system.

Disclosed and described, it is to be understood that this invention is not limited to the particular examples, process steps, and materials disclosed herein as such process steps and materials may vary somewhat. It is also to be understood that the terminology used herein is used for the purpose of describing particular embodiments only and not intended to be limiting since the scope of the present invention will be limited only by the appended claims and equivalents thereof. The following examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

The invention will be further described and illustrated in the following examples.

EXAMPLES

Cell Culture

Three main cell types of the cardiovascular system were evaluated: primary cardiomyocytes derived from neonatal rats primary vascular smooth muscle (VSM) cells derived from rat aorta and human umbilical vein endothelial cells. Furthermore, human colon carcinoma HT29 cells and BL6-8 melanoma cells were evaluated as representative cancer cells. The cells were prepared as described previously in Etzion S. et al.: JMCC 33 (2001) 1321-30; Granot Y. et al.: JBC 268 (1993) 9564-9; the ATCC (the Global Bioresource Center™); and Assa-Kunik et al.: J. Immunol. 171 (2003) 2945-52.

Western Immunoblot Assay

The active members of the MAPKs super-family were evaluated with specific antibodies against the phosphorylated site of the proteins. Confluent cell monolayers were growth-arrested in serum-free medium for 24 h prior to treatment with the compounds in this patent. Cells were washed twice with medium, scraped, resuspended in lysis buffer (10% glycerol, 25 mM NaCl, 0.1% Triton X-100, 50 mM NaF, 10 mM Na-pyrophosphate, 2 mM EGTA, 2 mM DTT, 20 mM p-nitrophenylphosphate, 25 mM Tris-HCl, 2 mM $Na_2VO_4$, 10 μM PMSF, 10 μg/ml Leupeptin), and the lysate was centrifuged at 14,000 rpm for 20 min. Samples were separated by SDS-polyacrylamide gel electrophoresis, transferred to nitrocellulose membrane, and blocked for 1 h at room temperature with 5% nonfat milk in TBS-T buffer (20 mM Tris, 500 mM NaCl, and 0.01% Tween 20). The membrane was then incubated overnight at 4° C. with an appropriate dilution of anti-phospho-ERKs or anti-total ERK, anti-phospho-p38 or anti-phospho-JNK, followed by incubation for 1 h with the appropriate horseradish peroxidase-conjugated secondary antibody. The immunoblot signal was visualized through enhanced chemiluminescence.

Cell Viability

The cell viability was examined using the XTT method following kit instructions (Biological Industry, Israel). The assay is based on the ability of metabolic active cells to reduce the tetrazolium salt XTT to orange colored compound of formazan. The dye formed is water soluble and the dye intensity can be read with spectrophotometer at 450-500 nm. The intensity of the dye is proportional to the number of metabolic active cells.

DNA Fragmentation

Apoptosis Assay

The various cell types were incubated with a compound of formula I (0.3-25 μM) for 24-48 h. Untreated cells were served as control. After trypsinization, cells were centrifuged for 5 min, 1500 g and resuspended in DMEM medium contains 10% FCS. Sample of the cells (25 μl) was added to 2 μl mixture of (5 μg/ml) ethidium bromide and (5 μg/ml) acridine orange in PBS. Sample of the stained cells was examined under fluorescent microscope. Ethidium bromide binds to the DNA of damaged cells and stains it orange, while acridine orange stains the nucleus in green. Apoptotic cells appear as nuclei with orange staining of fragmented DNA.

PI (Propidium Iodide) Staining

HT29 cells, either untreated or treated 48 h with a compound of formula I (25 μM), after trypsinization, were collected and centrifuged for 5 min, 800 g. The pellet was resuspended with PBS and centrifuged again. 60 μl of PBS was added to the pellet followed by addition of 360 μl of ice-cold 80% ethanol and incubating overnight at −20° C. The cells were thawed on ice and centrifuged for 5 min 800 g 4° C. After washing twice with PBS, 0.5 ml of staining solution (0.1% Triton 100× and 50 μg/ml RNase) was added for 16-18 h, 4° C. The cells were centrifuged and resuspended with 1 ml of staining solution contains PI (20 μg/ml). Analysis was carried out by fluorescence-activated flow cytometer (FACSscan).

Example 1

Synthesis of 2-chloro-3-(p-methylphenylamino)-1,4-naphthoquinone (TW-69)

p-Toluidin (1.4 g, 13.2 mmol) was added to the solution of 2,3-dichloro-1,4-naphthoquinone (1.0 g, 4.4 mmol) in ethanol (300 ml). The reaction mixture was allowed to stir at room temperature for over night. The precipitated product was filtered off and washed with cold ethanol. The product was purified by recrystallization with ethanol/$CHCl_3$ (1:5) to afford the fine reddish needles. Yield: 0.642 g (53.8%), Mp: 295° C.

Example 2

Synthesis of 2-chloro-3-(4-hydroxyphenylamino)-1,4-naphthoquinone (TW-73)

2,3-Dichloro-1,4-naphthoquinone (1.0 g, 4.4 mmol) was dissolved in 80 ml ethanol at 60° C., to which p-aminophenol (1.44 g, 13.2 mmol) in 20 ml ethanol was added. The reaction mixture was stirred at room temperature for 16 h. The precipitated product was filtered off and recrystallized from ethanol to afford pure purple crystals. Yield: 1.30 g (99%), Mp: 233° C.

Example 3

Synthesis of 2-pyrrolidine-3-(p-methylphenylamino)-1,4-naphthoquinone (TW-85)

To a solution of 2-chloro-3-(p-tolylamino)-1,4-naphthoquinone (0.1 g, 0.33 mmol) in 20 ml DMF were added 10 equivalents of pyrrolidine (0.23 ml). The reaction mixture was stirred at 50° C. for 24 h. The solvent was removed under reduced pressure and the deep blue crude product was purified twice on a silica gel (70-230 mesh) column chromatography, eluting with a mixture of n-hexane/EtOAC (9:1) to afford the pure title compound. Yield: 0.037 g (33.6%), Mp: 128-130° C.

Example 4

Synthesis of 2-pyrrolidine-3-(p-hydroxy-phenylamino)-1,4-naphthoquinone (TW-96)

To 2-chloro-3-(p-hydroxyphenylamino)-1,4-naphthoquinone (0.15 g, 0.49 mmol) were added 20 equivalents of pyrrolidine (0.84 ml). The reaction mixture was refluxed for 2 h. The excess pyrrolidine was removed under reduced pressure and the deep blue crude product was purified on a silica gel (70-230 mesh) column chromatography, eluting with a mixture of n-hexane/EtOAC (7:3) to afford a pure blue title compound. Yield: 0.067 g (40%), Mp: 145° C.

Example 5

Synthesis of N-[3-(1,4-dioxo-1,4-dihydro-naphthalen-3-ylamino)-phenyl]-benzamide (TW-61)

Benzoyl chloride (0.44 ml, 3.7 mmol) was added to a solution of the 1,3-phenylene diamine-1,4-naphthoquinone (1.0 g, 3.7 mmol) in ethanol (150 ml). The reaction mixture was stirred at room temperature for 24 h. The precipitate was filtered off, dissolved in DCM and isolated by silica gel column chromatography with EtOAC/n-hexane (1:5) as eluent. The solvent was removed under the reduced pressure and the product was recrystallized from CHCl$_3$ to obtain pure dark orange crystals. Yield: 0.53 g (39%), Mp: 185° C.

Example 6

Synthesis of 2-pyrrolidino-3-(4-acetylphenylamino)-9,10-naphthoquinone (EH-82)

2-Pyrrolidino-3-(4-hydroxyphenylamino)-9,10-naphthoquinone (TW-96) (0.05 g, 0.15 mmol) was dissolved in 2 ml of absolute ethanol, and 1 ml solution of potassium hydroxide in ethanol (solution prepared by dissolving 0.5 g KOH in 5 mL of absolute ethanol) was added dropwise while stirring. To this mixture were added 4 drops of acetic anhydride while stirring and the reaction mixture was allowed to stir for another 30 min. at room temperature. The ethanol was then vacuum evaporated, 10 ml of ethyl acetate added and the mixture paper filtered. The clear filtrate was twice washed with water, dried over anhydrous magnesium sulfate, filtered and the solvent removed. The remaining dark solid was recrystallized from an 1:1 mixture of ethyl acetate and hexane to yield dark shiny crystals of the title compound. Yield 74%.

Example 7

Synthesis of 2-chloro-3-(L-prolinemethyl ester)-1,4-naphthoquinone (EH-48)

2,3-Dichloronaphthoquinone (1 g, 4.4 mmol) and L-methyl praline (0.57 g, 4.4 mmol) where dissolved in absolute ethanol (20 mL) and the solution was allowed to stir at room temperature overnight, after which the orange-colored solid was recovered and washed with a small amount of cold ethanol. Yield 85%.

Example 8

Cell Viability of Cardiomyocytes, VSM Cells and Endothelial Cells

The viability of the cells was measured as described above. Briefly, cells were incubated with the compounds for 24 h followed by incubation with XTT for 4 h. The assay is based on the ability of metabolic active cells to reduce the tetrazolium salt XTT to orange colored compound of formazan. The intensity of the dye is proportional to the number of metabolically active cells. The concentration at which 50% cells remain viable, $ID_{50}$, is shown in Table 1 for several compounds of the invention.

TABLE 1

| $ID_{50}$ in µM for certain compounds of formula I | | | |
|---|---|---|---|
| | Cardiomyocytes | VSM cells | Endothelial cells |
| TW85 | >20 | 3.6 | 0.8 |
| TW96 | 0.4 | 0.2 | 0.5 |
| TW190 | 4.45 | 0.75 | 0.95 |
| TW193 | 3.75 | 0.85 | 0.95 |
| TW225 | >5 | 1.2 | >5 |

Example 9

MAPKs and STATs Signaling in VSM Cells

Figure 1A:
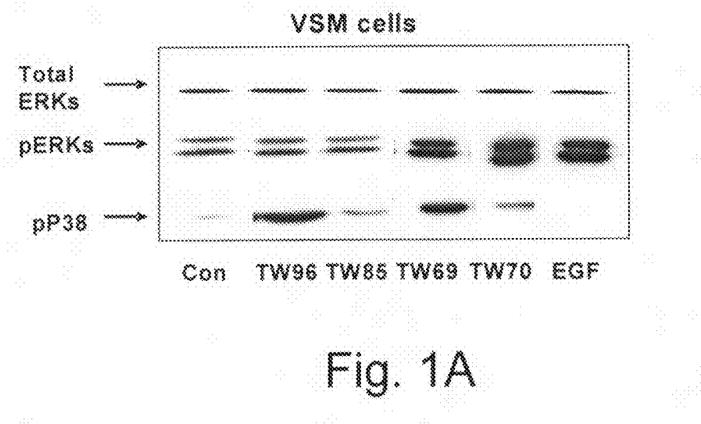
FIG. 1A shows MAPKs activation in VSM cells and FIG. 1B shows MAPKs activation in cardiomyocytes after the incubation with compounds of formula I.

Stimulation of ERKs and p38-MAPKs with compounds of the invention was characterized in VSM cells and cardiomyocytes. FIG. 1A shows the stimulation of ERKs and/or p38-MAPKs following incubation with TW69, TW70, TW85 and TW96 (0.5-20 µM, 20 min, 37° C.). The cells were harvested with lysis buffer and MAPKs stimulation was estimated using the western immunoblot analysis as described above. As a positive control for ERKs activation, the cells were incubated with $10^{-7}$M EGF for 5 minutes. The results indicate that TW69 stimulate both ERKs and p38-MAPKs signaling. However, TW-70 stimulates mainly ERKs signaling pathway, whereas TW96 stimulates mostly the P38-MAPK. Therefore, this compound and other derivates may be used as selective compounds to inhibit or stimulate one of the members in the MAPKs-signaling pathway.

Figure 2:
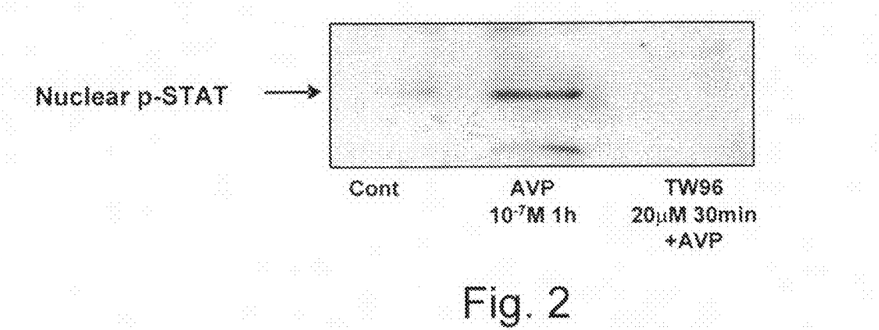
FIG. 2. is a Western immunoblot showing inhibition of the phosphorylated STAT3 after activation of VSM cells with AVP followed by treatment with compounds of formula I.

Interestingly, TW96 is a strong inhibitor of STAT3 phosphorylation, in addition to its being a modulator of MAPKs signaling (FIG. 2).

Example 10

MAPK Signaling in Cardiomyocytes

Figure 1B:
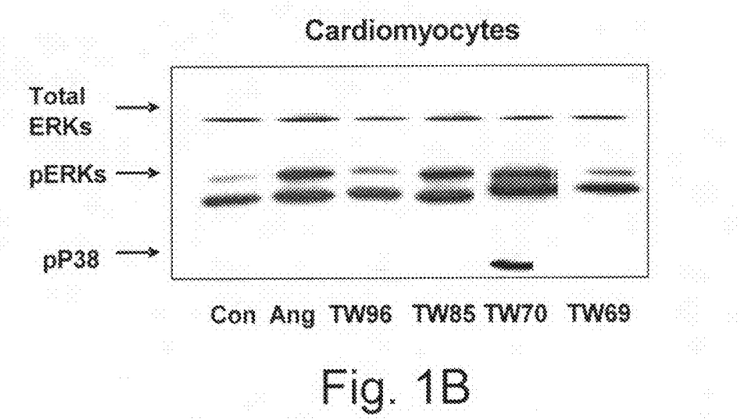

The effect of the compounds of formula I on ERKs and p38-MAPK was checked in cardiomycetes. Western immunoblot (FIG. 1B) shows the relative amounts of ERKs (42/44 kDa protein-doublet) and p38-MAPK following incubation with the compounds TW96, TW85, TW69 and TW70. Stimulation of the MAPKs members by compounds of the invention was compared with the stimulation by the growth factor Ang (Angiotensin II, 10 nM, 10 min), which is known as MAPKs stimulator in cardiomyocytes. Cardiomyocytes were starved for 24 h in serum free medium, afterwards incubated with the selected compound (0.5-10 µM) for 20 min, 37° C. Cells were harvested with lysis buffer, and MAPKs stimulation was estimated using the western immunoblot analysis as described. ERKs and p38 were related to the total amount of ERKs proteins in the sample. Compound TW85, e.g., stimulates the ERKs signaling pathway but not the p38-MAPK signaling pathway, as can be seen in FIG. 1B. The results indicate that some compounds stimulate both ERKs and p38-MAPK, but compounds such as TW85, TW69 stimulate mainly the ERKs signaling pathway without significantly influencing the p38-MAPK signaling pathway. These results are important when considering a possibility to increase the cell survival after myocardial infarction. As explained, the ERKs signaling pathway participate in the cell survival and proliferation. Administering the compounds stimulating this pathways after myocardial infarction may accelerate cell survival of the cardiomyoctes; alternatively, said compounds may be administered as a preventing drug before the injury occurs in risk cases.

Example 11

Viability of HT29 Human Colon Carcinoma Cells

HT29 human carcinoma cells were incubated for 24 h with compounds of the invention. Table 2 shows $ID_{50}$ in µM for some compounds.

TABLE 2

Carcinoma cell viabilities.

| | HT29-colon carcinoma |
|---|---|
| TW85 | 3.5 |
| TW185 | 0.65 |
| TW96 | 0.5 |
| TW190 | 1.0 |
| TW193 | 1.0 |

These results clearly show the ability of compounds of the invention, e.g. TW185 or TW96, to reduce the viability of human carcinoma cells, and indicate the therapeutic potential of the compounds for preventing uncontrolled proliferation of malignant cells.

Example 12

MAPKs Signaling in HT29 Colon Carcinoma Cells and BL6-8 Melanoma Cells

Figure 3A:
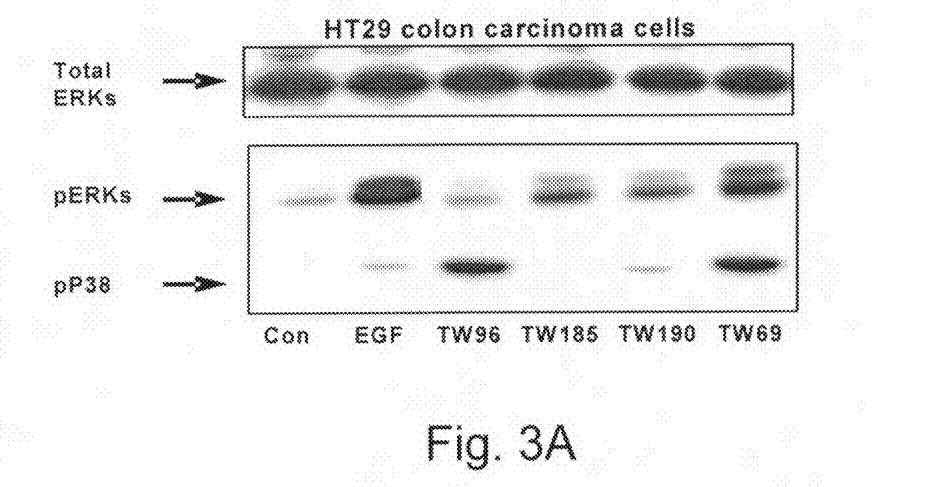
FIG. 3. is a Western immunoblot showing ERKs and p38 phosphorylation in (A) HT29 colon carcinoma cells and (B) BL6-8 melanoma cells after the incubation with compounds of formula I.
Figure 3B:
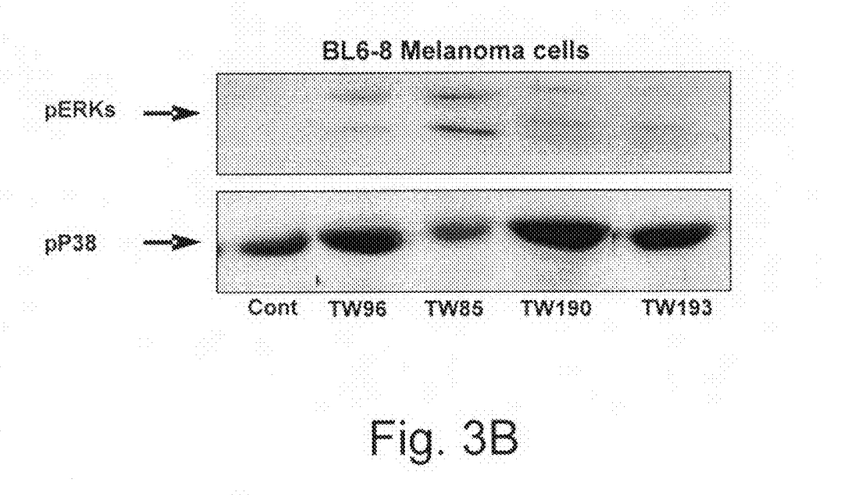

The effect of compounds of the invention on ERKs and p38-MAPK in human carcinoma HT29 cells was characterized. FIG. 3A demonstrates the stimulating effect of some compounds on ERKs (42/44 kDa) and p38. The effect of TW69, TW96, TW185 and TW190 was compared with the effect of the growth factor EGF (Epidermal growth factor, 1 nM, 10 min), which is known as ERKs stimulator in these cells. The cells were starved for 24 h in serum free medium, incubated with the selected compound (5-25 µM) for 20 min to 4 h (dependent on the compound examined), 37° C., harvested, centrifuged and suspended in the lysis buffer. The MAPKs stimulation was estimated using the western immunoblot analysis as described above. The blot shows ERKs and p38 phosphorylated proteins, as well as the total ERKs proteins in the sample. A compound of formula I, TW96 stimulates mostly the p38-MAPK signaling pathway. Therefore, this compound is useful for increasing the apoptotic response in human colon carcinoma cell death. In addition, in melanoma cells, compounds such as TW96, TW190 and TW193 specifically stimulate the P38 pathway without stimulating the ERKs survival pathway, suggesting that these compounds may be useful in inhibiting melanoma cell proliferation.

The results indicate the ability of the compounds, such as TW96, to stimulate the p38-MAPK signaling pathway without significantly influencing the ERKs signaling pathway, which enables to increase the mortality of malignant cells. As explained, the ERKs signaling pathway participates in cell proliferation, whereas p38-MAPK leads to apoptosis.

Example 13

Apoptosis of HT29 Human Colon Carcinoma Cells Following Incubation with TW69

Figure 4A:
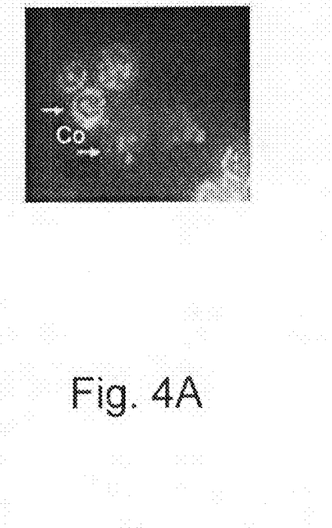
Figure 4B:
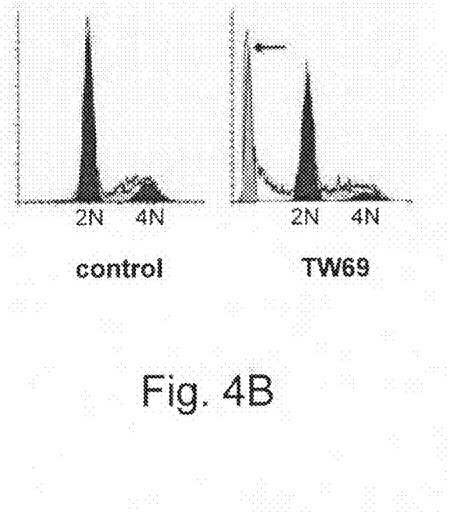

Apoptosis was evaluated following incubation of 48 h with compound TW 69 using DNA fragmentation method (ethidium bromide staining) and PI (propidium iodide) staining assay, as described above. Apoptotic cells appear as nuclei with orange staining of the DNA fragments (AP) compared to control (Co) cells in the ethidium assay. PI stains DNA in all of the cell cycle stages. Fragments of DNA were also stained with PI, therefore this assay recognized apoptotic cells (arrow in FIG. 4B). Black and white photo (FIG. 4A) shows the control cells as brighter and apoptotic cells as dimmer. The results indicate that TW69 accelerate the apoptotic response by 30%, showing the potential of the compounds as medicaments for treating malignancies.

While this invention has been described in terms of some specific examples, many modifications and variations are possible. It is therefore understood that within the scope of the appended claims, the invention may be realized otherwise than as specifically described.

Example 14

Detection of Cardiomyocyte Viability Following Incubation with EH48

Figure 5:
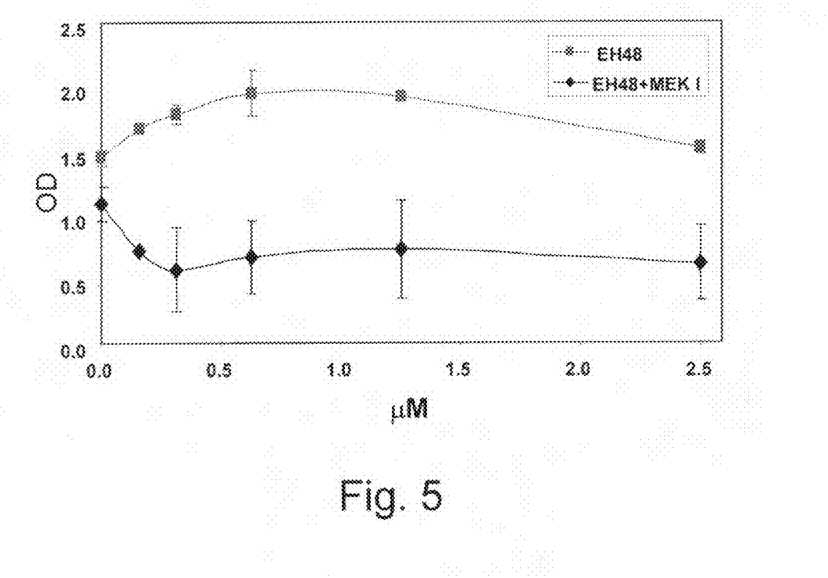
FIG. 5. shows XTT elevation in cardiomyocytes following incubation with compound of formula II (EH48); inhibition of MEK revealed an involvement of the ERKs pathway in the survival of cardiomyocytes.

The viability of the cells was measured as described above. Briefly, cells were starved for 16-18 h followed by incubation with the compound of formula II (EH48) for 24 h and incubation with XTT for an other 4 h. The assay is based on the ability of metabolic active cells to reduce the tetrazolium salt XTT to orange colored compound of formazan. The intensity of the dye is proportional to the number of metabolically active cells. Increased in dye intensity indicated an increase in cell survival and viability as shown in FIG. 5. Pre-incubation of the cells with the inhibitor of MEK1 revealed an involvement of the ERKs signaling pathway in cardiomyocyte survival.

Example 15

Cardiomyocyte Proliferation Following Direct Injection of EH48 In-Vivo

Figure 6A:
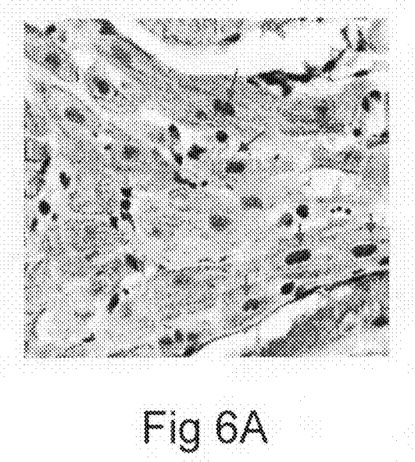
Figure 6B:
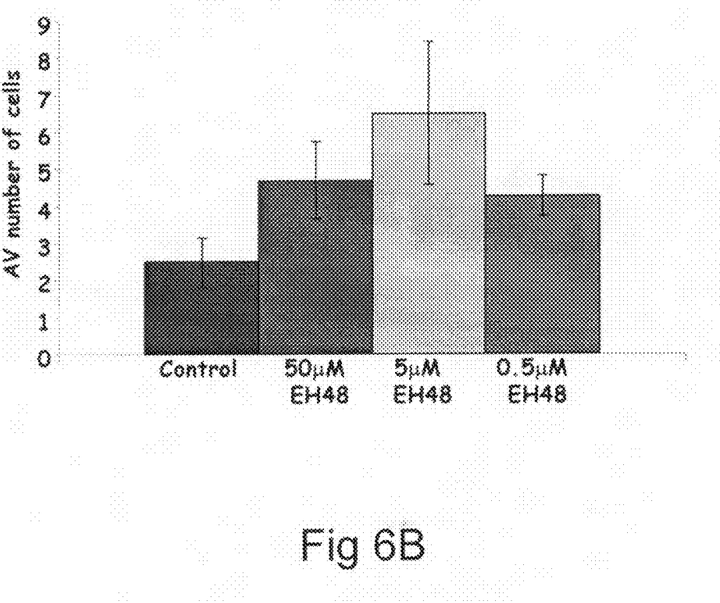

Proliferation of cardiomyocytes was evaluated in-vivo following direct injection of EH48 in three concentrations (0.5, 5 and 50 microM) into rat heart. Three days after injections rats were sacrificed and the hearts were fixed with formaldehyde 4%. Slides of 5 micron were stained with the DNA specific marker PCNA. Only cells with morphology of cardiomyocytes (large cells with striation) that expressed the PCNA in the nucleus (brown staining) were considered as proliferate cardiomyocytes (FIG. 6A, arrows). The number of stained cells in each treatment was evaluated compared to control (saline injected) rats (FIG. 6B).

These results indicate a positive in-vivo effect of EH48 on the survival and proliferation of cardiomyocytes.

While the invention has been described using some specific examples, many modifications and variations are possible. It is therefore understood that the invention is not intended to be limited in any way, other than by the scope of the appended claims.

The invention claimed is:

1. A method of treating cardiovascular disorder, involving increased survival and proliferation of cardiomycetes in a patient in need of such treatment, comprising administering a compound of formula II:

wherein the proline moiety is either L isomer or D isomer or a mixture of L isomer and D isomer, and $R_2$ is selected from $C_1$-$C_{16}$ alkyl.

2. A method according to claim 1, in which $R_2$ is methyl group.

* * * * *